(12) United States Patent
Yee et al.

(10) Patent No.: US 10,362,781 B2
(45) Date of Patent: *Jul. 30, 2019

(54) METHODS OF CONTROLLING THE BREEDING BEHAVIOR OF BUTTERFLIES

(71) Applicant: University of the West Indies, a Regional Institution, established by Royal Charter, St. Augustine (TT)

(72) Inventors: Trevor Herbert Yee, Kingston (JM); Charah Tabetha Watson, Kingston (JM); Eric Garraway, Kingston (JM)

(73) Assignee: University of the West Indies, a Regional Institution, established by Royal Charter, St. Augustine (TT)

( * ) Notice: Subject to any disclaimer, the term of this patent is extended or adjusted under 35 U.S.C. 154(b) by 0 days.

This patent is subject to a terminal disclaimer.

(21) Appl. No.: 14/801,301

(22) Filed: Jul. 16, 2015

(65) Prior Publication Data
US 2016/0021878 A1 Jan. 28, 2016

Related U.S. Application Data

(63) Continuation of application No. 13/576,080, filed as application No. PCT/IB2011/000440 on Jan. 28, 2011, now Pat. No. 9,113,635.

(60) Provisional application No. 61/299,125, filed on Jan. 28, 2010.

(51) Int. Cl.
| | | |
|---|---|---|
| *A01N 27/00* | (2006.01) | |
| *A01N 65/08* | (2009.01) | |
| *A01N 43/30* | (2006.01) | |
| *A01N 65/00* | (2009.01) | |
| *A01N 65/36* | (2009.01) | |

(52) U.S. Cl.
CPC ............ *A01N 27/00* (2013.01); *A01N 43/30* (2013.01); *A01N 65/00* (2013.01); *A01N 65/08* (2013.01); *A01N 65/36* (2013.01)

(58) Field of Classification Search
CPC .... A01N 2300/00; A01N 27/00; A01N 65/00; A01N 65/36
USPC ...................................... 424/45, 84; 514/464
See application file for complete search history.

(56) References Cited

U.S. PATENT DOCUMENTS

| | | | | |
|---|---|---|---|---|
| 5,506,251 | A * | 4/1996 | Thirugnanam | A01N 37/28 514/383 |
| 2007/0020305 | A1* | 1/2007 | Nansen | A01N 27/00 424/410 |
| 2009/0246302 | A1 | 10/2009 | Pathipati et al. | |
| 2010/0303940 | A1* | 12/2010 | Enan | A01N 37/02 424/778 |

OTHER PUBLICATIONS

Encyclopædia Britannica. Lepidopteran [online],Feb. 1997 [retrieved on Dec. 14, 2017]. Retrieved from the Internet< URL:https://www.britannica.com/animal/lepidopteran>.*
Anderson, et el., "Larval Diet Influence on Oviposition Behaviour in Spodoptera Littoralis", Entomologia Experimentalis et Applicata, 74:71-82, Jan. 1995, 13 pages.
Craighead, "Popular and Practical Entomology", The Canadian Entomologist, 55(4):76-79, Apr. 1923, 5 pages.
Hokkanen, "Trap Cropping in Pest Management", Ann. Rev. Entomol, 36:119-138, No Month Given 1991, 22 pages.
Honda, "Identification of Host-Plant Chemicals Stimulating Oviposition by Swallowtail Butterfly", Journal of Chemical Ecology, 16(2):325-337, Feb. 1990, 13 pages.
International Search Report and Written Opinion issued in PCT/IB2011/000440, dated Aug. 30, 2011, 12 pages.
Parmar, V. et al., "Phytochemistry of the Genus Piper", Phytochemistry, 46(4):597-673, Oct. 1997, 77 pages.
Penz, et al., "Interaction between Papilio Hectorides (Papilionidae) and Four Host Plants (*Piperaceae rutaceae*) in Southern Brazilian Population", Journal of Research on the Lepidopiera, 29(1-2):161-171, No Month Given 1990, 11 pages.
Prudic, et al., "The Signal Environment is More Important than Diet or Chemical Specialization in the Evolution of Warning Coloration", PNAS, 104(49):19381-19386, Dec. 4, 2007, 50 pages.
Saxena, et al., "Host-Plant Relations of the Citrus Butterfly *Papilio demoleus* L.: Orientation and Ovipositional Responses", Entomologia Experimentalis et Applicata, 24(1):1-10, Jul. 1978, 11 pages.
Thompson, "Preference Hierarchies and the Origin of Geographic Specialization in Host Use in Swallowtail Butterflies", Evolution, 47(5):1585-1594, Oct. 1993, 11 pages.

(Continued)

*Primary Examiner* — Ali Soroush
*Assistant Examiner* — Courtney A Brown
(74) *Attorney, Agent, or Firm* — Wilmer Cutler Pickering Hale and Dorr LLP

(57) ABSTRACT

Methods of controlling the feeding and/or breeding behavior of a target insect are disclosed in which a host plant is provided a substantial distance from a plant of interest, chemical attractant that induces the target insect to lay eggs on the host plant is applied to the host plant, application of the chemical attractant to the host plant is repeated as required to induce residual target-insect populations to lay eggs on the host plant, and wherein the behavior is controlled when a substantial number of offspring belonging to subsequent generations themselves mature and display a preference for laying eggs on the same type of host plant on which they were reared without further application of the chemical attractant is provided. Also disclosed are methods of deterring target insect feeding and breeding on plants of interest by applying toxic plant extract to the plants of interest.

21 Claims, 3 Drawing Sheets

(56) References Cited

OTHER PUBLICATIONS

Wiklund, "Oviposition Preferences in Papilio Machaon in Relation to the Host Plants of the Larvae", Entomologia Experimentalis et Applicata, 17(2):189-198, Jun. 1974, 11 pages.
Adams, Robert P. "Identification of Essential Oil Components by Gas Chromatography/Quadrupole Mass Spectroscopy. Part B—Appendicies I and II" Baylor University, Allured Publishing Corporation. Pates 9-40, No Month Listed 2001. ISBN 0-931710-85-5. 35 pages.

* cited by examiner

METHODS OF CONTROLLING THE BREEDING BEHAVIOR OF BUTTERFLIES

CROSS-REFERENCE TO RELATED APPLICATIONS

This application is a continuation of U.S. patent application Ser. No. 13/576,080, filed Oct. 22, 2012, entitled "Methods of Controlling the Breeding Behavior of Butterflies"; which is a National Phase application of International Application No. PCT/IB11/00440, filed Jan. 28, 2011, entitled "Methods of Controlling the Breeding Behavior of Butterflies"; which claims the benefit of priority to U.S. Provisional Application No. 61/299,125, filed Jan. 28, 2010, entitled "Methods of Controlling the Breeding Behavior of Butterflies", the content of which are hereby incorporated by reference, in their entirety.

BACKGROUND

The Citrus Swallowtail butterfly, *Heraclides andraemon* Hubner, was first observed in Jamaica in 1945. Since its arrival, it has become the most predominant citrus-plant feeding swallowtail butterfly on the island. As a result, it has become a significant pest of citrus plants, especially nurseries. Young seedlings are particularly vulnerable, as they are less capable of surviving having their leaves eaten by butterfly larvae compared to mature citrus plants. The butterflies prefer local species of citrus plants, such as lime plant and orange plant. Their consumption of citrus plants is costly and wasteful, which makes them a tremendous pest to the citrus industry.

Measures taken by the industry to prevent attack on citrus plant nurseries thus far have proved expensive, ineffective, and in some instances, deleterious to the environment. These methods include spraying, hand removal, and the use of physical barriers such as netting.

SUMMARY

Methods of using a chemical attractant to control the feeding and breeding behavior of target insects are disclosed. A host plant, which generally contains an attractant for the target insect and is capable of supporting target insect offspring to control egg laying, is provided a substantial distance from a plant of interest. The plant of interest is one in which target insects are naturally attracted to feeding or breeding on in the wild, but is commercially or aesthetically valuable and therefore desirable of protecting from target insects that would harm it. No chemical attractant is applied to the plant of interest. The host plant and plant of interest may share a common chemical that acts as an attractant to the target insect. The chemical attractant is applied to the host plant and induces target insects to lay eggs on it. The emerging juveniles feed on the host plant and, based on the tendency of these insects to breed on the same type of plant on which they were reared, they lay the next generation of eggs on the same host plant species. The behavior of the target insect is controlled, for example, when a substantial number of mature offspring lay eggs on the same type of host plant on which they were reared without repeat application of the chemical attractant.

In one aspect, the method includes inducing *H. andraemon* that are bred on lime plant to lay eggs on *Piper amalago* var. *amalago* plant. *H. andraemon* naturally prefer to breed on the type of plant on which they were reared. Therefore, using this method results in an effective control measuring by which the egg-laying preference is maintained from one generation to the next. By applying *Piper amalago* var. *amalago* plant oil, lime plant oil, limonene, or d-limonene in sufficient amounts to *Piper amalago* var. *amalago* plant, *H. andraemon* are shown to prefer to feed and breed on *Piper amalago* var. *amalago* plant to lime plant.

In one aspect, a kit useful for controlling insect egg laying and/or feeding is disclosed, which comprises a chemical attractant to attract a targeted insect. The chemical attractant can be selected from the group consisting of *Piper amalago* var. *amalago* plant oil, limonene, d-limonene, lime plant oil, or a combination thereof; an agriculturally acceptable carrier; and instructions for applying the chemical attractant to a host plant to induce egg laying or feeding on the host plant instead of a plant of interest. The instructions direct that the host plant be provided a particular distance from the plant of interest. In another aspect, the host plant is a *Piper* plant that contains limonene or d-limonene.

In any one of the above embodiments, providing the host plant consists of planting enough of the host plant to support the egg-laying and feeding of a target insect population.

In one or more embodiments, the behavior is controlled when 50% or more of the offspring belonging to subsequent generations themselves mature and display a preference for laying eggs on the same type of host plant on which they were reared without further application of the chemical.

In one or more embodiments, the application of the chemical attractant to the host plant is repeated as required to induce residual target-insect populations to lay eggs on the host plant.

In another aspect, a kit useful for controlling insect egg laying and/or feeding is disclosed, and comprises a toxic extract for deterring target insects from laying eggs or feeding on a plant of interest. The toxic extract can be derived from any plant containing a compound that has toxic effects on target insects. Specific examples of plants include, but are not limited to, *Piper* spp. such as *Piper aduncum*, *Piper amalago* var. *amalago*, *Piper hispidum*, *Piper fadyenii*, and *Piper nigrinodum*.

In another aspect, a kit for repelling the feeding of target insect larvae is disclosed. The kit provides a chemical attractant derived from a plant of interest. It also includes instructions for applying the chemical attractant to a host plant. Using this kit, gravid female target insects are induced to lay eggs on the host plant, and because the target insects prefer to lay eggs on the type of plant on which they were bred, the offspring of induce gravid females will overwhelmingly prefer to feed and breed on the type of host plant on which they were laid.

In one or more aspects, the instructions direct the application of the chemical attractant to the host plant, or the extract to the plant of interest at least once daily, twice daily, weekly, twice weekly, or at least once monthly.

In one or more of the above embodiments, the instructions direct providing enough of the host plant to support the egg-laying and feeding of a target insect population.

In any one of the above embodiments, the target insect is a species of butterfly.

In any one of the above embodiments, the target insect is a species of citrus swallowtail butterfly.

In any one of the above embodiments, the target insect is selected from a group consisting of *Heraclides* (syn. *Papilio*) *andraemon* Hubner, *Heraclides andraemon: bonhotei* Sharpe, *Heraclides andraemon: andraemon* Hubner, *Heraclides andraemon: hernandezi* de la Torre, *Heraclides andraemon: tailori* Rothschild & Jordan, *Heraclides cresphontes* Cramer, *Heraclides hectorides* Esper, *Heraclides*

*thoas* L., *Heraclides thoas: brasilensis* Rothschild & Jordan, *Heraclides thoas: melonius*, Rothschild & Jordan, and *Heraclides thersites*, Fabricius.

In any one of the above embodiments, the chemical attractant is detectable by the target insect.

In the embodiment in which the toxic extract is used as a repellant, the toxic extract is detectable by the target insect.

In the embodiment in which the toxic extract is used as a pesticide, the toxic extract may or may not be detectable by the target insect.

In one or more embodiments, the chemical attractant comprises oil derived from a host plant that contains limonene or d-limonene. The chemical attractant can also be derived from a citrus plant.

In one or more of the embodiments, the chemical attractant comprises oil derived from the plant of interest, wherein the plant of interest is selected from the group consisting of *Citrus aurantifolia* (Christm.) Swingle (Rutaceae), *Piper amalago* var. *amalago* L. (Piperaceae), lime, *C. limon* (L.) Burm. F., lemon, *C. sinensis* (L.) Osbeck, sweet orange, *C. reticulata* Blanco, Mandarin orange, tangerine, *C. paradisi* Macf., grapefruit, *C. medica* L., citron, *C. aurantium* L. Seville orange, *C. grandis* (L.) Osbeck, shaddock, pummelo, *C. maxima* (Burm.) Merr, ugli, *C. reticulata* Blanco×*C. sinensis* (L.) Osbeck, ortanique, *C. mitis* Blanco, calamondin, *Fortunella margarita* Lour. Swingle, kumquat (Rutaceae), *Amyris* P. Browne Rutaceae), *Zanthoxylum* L., *Zanthoxylum martinicense* (Lam.), *Lantana camara, Jatropha podagrica, Canna indica*, and *Z. pterota* L. (Rutaceae).

In one or more of the embodiments, the plant of interest is a variety of citrus plant. The host plant can also be a *Piper* plant that contains limonene or d-limonene.

In any one of the above embodiments, the chemical attractant comprises limonene or d-limonene.

In one or more of the above embodiments, the agent is an aerosol mixture comprising the chemical attractant, the agriculturally acceptable carrier, butane, and propane.

In one or more embodiments, the aerosol consists of butane, propane, and chemical attractant derived from limonene or d-limonene.

In one or more embodiments, the amount of chemical attractant in the aerosol mixture is about 0.01%-0.05%; 0.05%-0.10%, 0.15%-0.20%; 0.20%-0.25%; 0.25%-0.30%; 0.30%-0.35%; 0.35%-0.40%; 0.40%-0.45%; or 0.45%-0.50% by weight.

In any one of the above embodiments, the amount of limonene, d-limonene, *Piper amalago* var. *amalago* plant oil, lime plant oil, or a combination thereof, is sufficient to attract the target insect.

In any one of the embodiments, the application consists of dipping, spraying, coating, diluting, covering, saturating, misting, fumigating, or dusting the host plant with the chemical attractant in an amount sufficient to affect the egg-laying behavior of the target insect.

In one aspect a pest control agent includes a chemical attractant selected from the group consisting of the *Piper amalago* var. *amalago* plant oil, limonene, d-limonene, lime plant oil, and a combination thereof; and an agriculturally acceptable carrier.

In one or more embodiments, the distance between the host plant and plant of interest is less than or equal to two kilometers.

In another aspect, target insect populations are controlled by applying a toxic extract to plants of interest. The toxic extract causes deformity or death when target insects ingest or come into physical contact with it. Toxic extract is derived from plants that contain toxin and no chemical attractant, or from host plants, which contain attractant and a chemical that is toxic to target insects. The toxic extract can be used in at least two ways to control the behavior of target insect populations. In one embodiment, the toxic extract is applied to a plant of interest and acts as a repellent by deterring target insects from feeding or breeding on the plant of interest. In another embodiment, the toxic extract is applied directly to eggs and larvae of target insects as a pesticide to kill or deform target insects.

In any one of the above embodiments, the toxic extract is derived from a plant selected from the group consisting of *Piper amalago* var. *amalago* L. (Piperaceae), *Piper aduncum, Piper hispidum, Piper fadyenii, Cleome rutidosperma* (Capperaceae), *Pentas* spp. (Rubiaceae), *Lantana camara* (Verbenaceae), *Canna indica* ((Cannaceae), *Kalanchoe crassula* (Crassulaceae), *Pimenta dioica* (Myrtaceae), *Peperomia pellucida* (Piperaceae), *Phyllanthus amarus* (Euphorbiaceae), *Pilea microphylla: microphylla* (Urticaceae), *Oxalis corymbosa* (Oxalidaceae), *Begonia* sp. (Begoniaceae), and *Dracaena sandariana* (Liliaceae) (Chinese bamboo).

In one or more embodiments, the toxin in the toxic extract is derived from a *Piper* plant. The *Piper* plant can be, for example, *Piper aduncum*.

In another aspect, a pest control agent includes a toxic extract derived from a plant containing a toxin, which causes death or deformity in target insects when ingested an agriculturally acceptable carrier, and in some embodiments, limonene, or d-limonene.

In one embodiment of this aspect, the toxic plant is *Piper aduncum*.

One aspect is a method of controlling a target insect population comprising applying to a host plant an extract from a plant that contains a toxin, to deter target insects from laying eggs on the host plant.

In one or more aspects, the toxin or agent is apiol.

In one or more aspects, the toxin is in the form of an emulsion comprising apiol, ethanol, and an agriculturally acceptable carrier.

In one or more aspects, the amount of toxin in the emulsion is about 0.1%-0.5%; 0.5%-1.0%, 1.0-1.5%, 1.5%-2.0%, 2.0%-2.5%, 2.5%-3.0%, 3.0%-3.5%, 3.5%-4.0%, 4.0%-4.5%, 4.5%-5.0%, 5.0%-5.5%, 5.5%-6.0%, 6.0%-6.5%, or 6.5%-7.0% by weight.

The advantages of using the disclosed methods, pest control agents, and kits are that they are useful natural and effective methods for controlling the feeding and breeding behavior of target insects. Specifically, the method, pest control agent, and kit are advantageous as natural and effective methods for controlling the feeding and breeding behavior of citrus plant-feeding butterflies.

BRIEF DESCRIPTION OF THE DRAWINGS

It is to be understood that while the embodiments have been described in conjunction with the detailed description thereof, the foregoing description is intended to illustrate and not limit the scope of the embodiments, which is defined by the scope of the appended claims. Other aspects, advantages, and modifications are within the scope of the following claims.

DEFINITIONS

Figure 1:
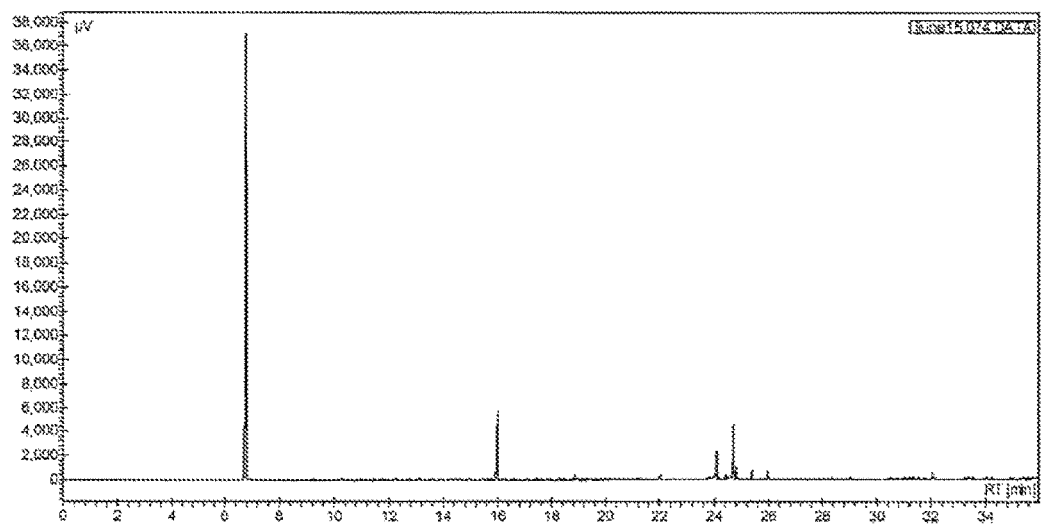
FIG. 1 is an image of a gas chromatograph of lime plant essential oils.

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The articles "a" and "an" are used herein to refer to one or to more than one (i.e., to at least one) of the grammatical object of the article. By way of example, "an element" means one element or more than one element.

The term "or" was used herein to mean, and was used interchangeably with, the term "and/or," unless context clearly indicates otherwise.

"Agriculturally acceptable carrier," as that term is used herein, is a medium that is suitable for delivery of the population control composition. The medium generally is compatible with active ingredients and excipients of the population control composition and has a benign effect on the environment. The excipient may be a wetting agent, spreading agent, deposit builder, adhesive, emulsifying agent, deflocculating agent, water modifier, or similar agent with or without toxic properties of its own. The excipient is intended to be used with the active ingredient as an aid to its application or to its effect.

"Chemical attractant," as that term is used herein, means the oils, such as the essential oils, obtained from a plant of interest by chemical, physical, or mechanical means. The chemical attractant is known to be attractive to the target insect. It affects the feeding and breeding behavior of target insects. Chemical attractants can be derived from plants of interest or host plants.

"Host plant," as that term is used herein, is a plant that is a host plant for the target insect; it is naturally attractive to target insects. In some instances, the host plant is selected by the target insect for egg laying and the host plant serves as a source of food for the emerging larvae. The host plant typically does not possess commercial or aesthetic properties that impart value to the plant. It is used in the methods disclosed herein to protect plants possessing commercial or aesthetic properties by serving as an alternative food source for target insects. The host plant may or may not be one that is naturally attractive to the target insect, but in the case in which it is not naturally attractive, it can be made attractive by application of certain chemical attractants. In some instances, the host plant is not a source of food for the target insect. The host plant and plant of interest may or may not share a common chemical that acts as an attractant to the target insect.

"Target Insect," as that term is used herein, is an insect that is naturally attracted to the plant of interest and for which it is desired to implement a measure of population control. Typically, the desire for population control arises from the damage inflicted on the plant of interest by the target insect. The term 'target insect' encompasses the insect at all stages of development and its offspring, including the mature insect, eggs, pupae stage, and larvae.

"Pest control agent," as that term is used herein, means an ingredient or a composition containing an ingredient that controls the population of a target insect. Population control can be accomplished in a variety of ways, including interruption of the feeding and/or breeding cycle of the target insect. In some embodiments, the pest control agent can serve as an attractant (for example, attracting the target insect away from the plant of interest or inducing female target insects to lay eggs on or consume plants treated with the attractant). In other embodiments, the pest control agent is used as a deterrent (for example, repelling the target of interest from the plant of interest).

"Plant of interest," as that term is used herein, is a plant to which target insects are naturally attracted to feeding or breeding. The plant of interest has commercial or aesthetic properties that make it a desirable plant to protect from the harmful effects of feeding and breeding target insects.

"Toxin," as that term is used herein, is a chemical derived from a plant that causes death or deformity in target insects that ingest or are otherwise exposed to the chemical. It also serves as a repellant (for example, repelling the target of interest from the plant on which the toxin is applied).

"Toxic extract," as that term is used herein, means the oils, such as the essential oils, obtained from a host plant that contains, in addition to chemical attractant, compounds that deter target insects from feeding or breeding on the plant to which the extract is applied. Toxic extract can also be derived from plants that contain toxic chemicals but no chemical attractant. The extract can be obtained by chemical, physical, or mechanical means. It is capable of causing death or deformity in a target insect if ingested.

DETAILED DESCRIPTION

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

The methods and products described herein relate to the use of chemical attractants and/or toxic extract to control the breeding behavior of insects, such as butterflies.

The methods involve using chemical attractants to control the egg-laying behavior of target insects. A host plant is provided as a food source for larvae, and is placed a particular distance from a plant of interest desired to be protected from feeding target insects. The distance is small enough to allow the host plant to be an alternate food source and/or breeding site for the target insects. However, the actual distance will depend on the individual foraging patterns of particular insect species, migration patterns of a particular insect species, ambient conditions, and the type of applicator used. In some embodiments, the host plants may be a distance of about 10 or more kilometers from the plant to be protected. When the target insect is a butterfly, and in particular a butterfly of the species *H. andraemon*, the distance between the host plant and plant of interest may be up to one to two kilometers apart.

Also disclosed is a pest control agent for attracting the feeding and breeding of target insects. In this aspect, the pest control agent comprises *Piper amalago* var. *amalago* plant oil, lime plant oil, limonene, d-limonene, or a combination thereof. It further comprises an agriculturally acceptable carrier. In one embodiment, the pest control agent is an aerosol mixture, and is applied to the host plant by spraying the mixture onto the host plant.

A kit useful for controlling insect egg laying or feeding on a plant is also disclosed. The kit contains chemical attractant in an agriculturally acceptable carrier and instructions for applying chemical attractant to a host plant to induce the target insects to lay eggs or feed on the host plant instead of nearby plants of interest.

In one or more embodiments, the chemical attractant is an extract from the host plant, which is known to be an attractant for the target insect. In other embodiments, the chemical attractant is a concentrated or purified component of the plant extract that is enriched in the chemical attractant. When the chemical attractant is applied to the host plant in amounts greater than naturally occurring levels found in nearby plants, the majority of gravid females prefer to lay eggs on host plants treated with the chemical attractant to nearby untreated plants. For some target insects known to prefer to lay and breed on citrus plants, the chemical attractant contains limonene or d-limonene.

Using chemical attractant to control target insect feeding and egg laying is advantageous because it is a natural and effective method of controlling the feeding and breeding behavior of insects such that the feeding and breeding can be redirected from a valuable or aesthetic crop to a less valuable crop. Valuable and aesthetic crops are thereby allowed to thrive and are not consumed by target insects.

Certain insects display a natural tendency to prefer to breed on the same type of plant on which they were reared. By inducing preferential egg laying of target insects on the host plant instead of the plant to be protected, subsequent generations exhibit a preference towards feeding and laying eggs on the host plant, thereby controlling the egg laying behavior of the target insect population. The behavior of the insects is controlled when a substantial number, e.g., a majority, of offspring belonging to subsequent generations themselves mature and display a preference for laying eggs on the same type of host plant on which it was reared without further application of the chemical attractant. In one or more embodiments, more than 50% of the subsequent generation displays a preference for laying eggs on the same type of host plant on which they were reared. In one or more embodiments, more than 55%, more than 60%, more than 65%, more than 70%, more than 75%, more than 80%, more than 85%, more than 90%, or more than 95% display a preference for laying eggs on the same type of host plant.

Chemical attractant is applied to the host plant to initially attract target insects and induce gravid females to lay eggs on it. When the offspring emerge, they feed on the host plant on which they were hatched, and develop a preference for laying their eggs on that particular type of host plant. For the majority of target insects, this preference for laying eggs on the same type of plant on which they were reared is maintained without reapplication of the chemical attractant.

In a particular embodiment, the target insects are a species of butterfly. In another embodiment, the target insects are gravid female butterflies. Particularly, the target insects are Citrus Swallowtail butterflies, otherwise known as *Heraclides* (syn. *Papilio*) *andraemon*. In another embodiment, the target insects are *Heraclides andraemon: bonhotei* Sharpe, *Heraclides andraemon: andraemon* Hubner, *Heraclides andraemon: hernandezi* de la Torre, *Heraclides andraemon: tailori* Rothschild & Jordan, *Heraclides cresphontes* Cramer, *Heraclides hectorides* Esper, *Heraclides thoas* L., *Heraclides thoas: brasilensis* Rothschild & Jordan, *Heraclides thoas: melonius*, Rothschild & Jordan, and *Heraclides thersites*, Fabricius.

The host plant is used to provide a place for target insects to lay eggs, and to provide food for larvae when the eggs hatch. Generally, the host plant contains an attractant that causes target insects to feed or lay eggs on it. The host plant is also capable of supporting the offspring of target insects. Any plant observed as a food source for target insects is an appropriate host plant. Suitable host plants have little or no commercial value, or are not susceptible to harm by butterflies feeding on their leaves. The host plant can be one of, or a combination of, a variety of plants. For *H. andraemon*, this plant contains the chemical attractant limonene or d-limonene. For instance, the host plant can be *Piper amalago* var. *amalago* plant, because *H. andraemon* has been observed to feed on *Piper amalago* var. *amalago* plant in the wild, and *Piper amalago* var. *amalago* plant contains d-limonene (see Table 1A). Citrus plants also contain d-limonene (see Table 1B). Of course, because citrus plants also contain d-limonene and *H. andraemon* feed on citrus plants in the wild, citrus plants can also be host plants. Specific examples of host plants for *H. andraemon* include *Piper amalago* var. *amalago* L. (Piperaceae), *Citrus aurantifolia* (Christm.) Swingle (Rutaceae), lime, *C. limon* (L.) Burm. F., lemon, *C. sinensis* (L.) Osbeck, sweet orange, *C. reticulata* Blanco, Mandarin orange, tangerine, *C. paradisi* Macf., grapefruit, *C. medica* L., citron, *C. aurantium* L. Seville orange), *Zanthoxylum* L., and *Zanthoxylum martinicense* (Lam.).

The plant of interest is likely naturally attractive to target insects, typically is of commercial or aesthetic value in some respect, and is therefore in need of protection from feeding and breeding target insects. For the species of butterflies known to feed and lay eggs on citrus plants, the plant of interest can be a plant from the citrus family. The plant of interest can be, for e.g., *Citrus aurantifolia* (Christm.) Swingle (Rutaceae), *Piper amalago* var. *amalago* L. (Piperaceae), lime, *C. limon* (L.) Burm. F., lemon, *C. sinensis* (L.) Osbeck, sweet orange, *C. reticulata* Blanco, Mandarin orange, tangerine, *C. paradisi* Macf., grapefruit, *C. medica* L., citron, *C. aurantium* L. Seville orange, *C. grandis* (L.) Osbeck, shaddock, pummelo, *C. maxima* (Burm.) Merr, ugli, *C. reticulata* Blanco×*C. sinensis* (L.) Osbeck, ortanique, *C. mitis* Blanco, calamondin, *Fortunella margarita* Lour. Swingle, kumquat (Rutaceae), *Amyris* P. Browne Rutaceae), *Zanthoxylum* L., *Zanthoxylum martinicense* (Lam.), *Lantana camara*, *Jatropha podagrica*, *Canna indica*, or *Z. pterota* L. (Rutaceae). The host plant and the plant of interest can be the same or different species of plant. The difference is that the chemical attractant is applied to the host plant to induce egg laying and feeding on the host plant to protect the plant of interest from these insect activities.

The chemical attractant in the host plant can be the same chemical attractant found in the plant of interest. For example, the host plant may naturally produce the chemical attractant at lower levels than the plant of interest, which can cause target insects to be less attracted to the host plant in its natural state compared to plants of interest with naturally higher levels of chemical attractant. Therefore, chemical attractant is applied to host plants to make them more attractive to feeding and egg-laying target insects, and to induce the insects to lay eggs on it. For example, the chemical attractant applied to the host plant can be derived from a plant containing limonene or d-limonene. More specifically, the chemical attractant can be derived from a citrus plant such as lime plant, *Piper amalago* var. *amalago* plant, or it can be an isolated component such as limonene or d-limonene.

According to one or more embodiments, host plant *Piper amalago* var. *amalago* can be treated with lime plant oil. Alternatively, *Piper amalago* var. *amalago* plant can be treated with *Piper amalago* var. *amalago* plant oil or isolated limonene or d-limonene. The treated *Piper amalago* var. *amalago* plant is placed a distance from a plant of interest, e.g., lime plant. A mixture containing chemical attractant in the form of, e.g., an aerosol mixture, is applied to *Piper amalago* var. *amalago* plant in an amount sufficient to induce a number of target insects to feed or breed on *Piper amalago* var. *amalago* plant instead of lime plant. The distance between the *Piper amalago* var. *amalago* plant sprayed with, e.g., lime plant oil, and the plant of interest, is small enough to attract a substantial number of target insects to feed or breed on the *Piper* plant instead of the lime plant, but great enough to help prevent inadvertent application of the oil containing chemical attractant to the plant of interest. For example, the distance can be as great as 10 or more kilometers, or as small as two meters, depending upon foraging patterns of a particular insect, the migration distances of a particular insect, ambient conditions, and the type of applicator used.

The number of treated host plants should be sufficient to support the target population in the area.

Figure 2:
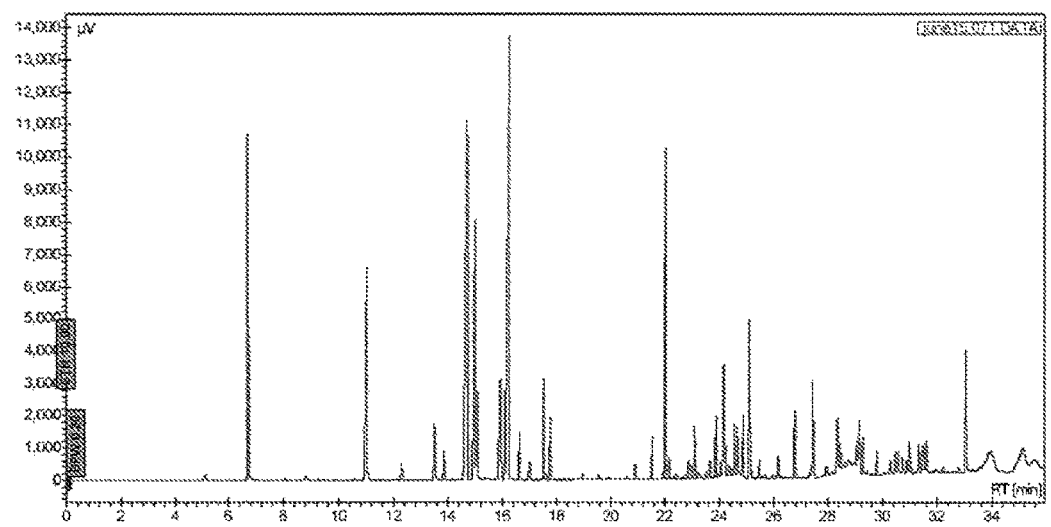
FIG. 2 is an image of a gas chromatograph of *Piper amalago* var. *amalago* plant essential oils.
Figure 3:
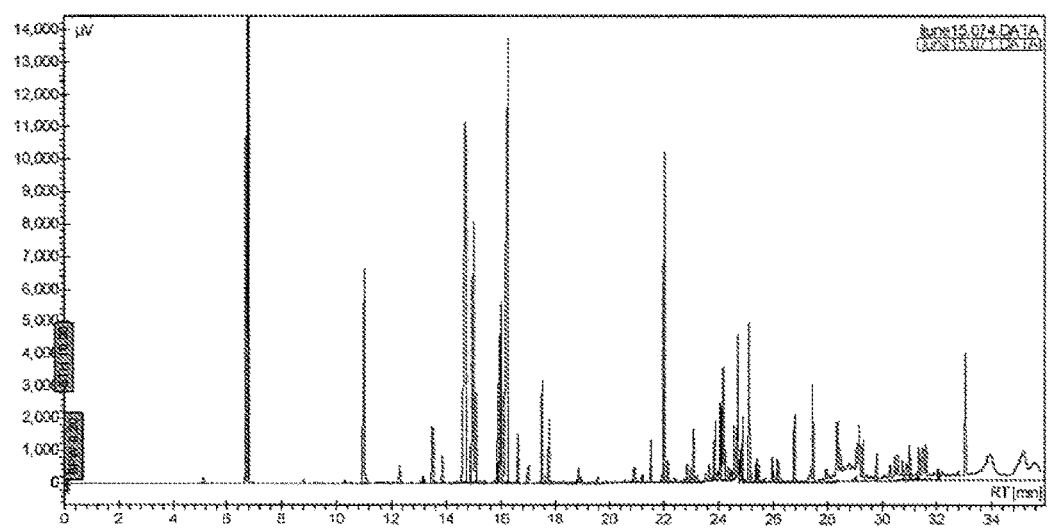
FIG. 3 is an image of superimposed gas chromatographs of lime plant and *Piper amalago* var. *amalago* plant essential oils.

*H. andraemon* is naturally attracted to feeding and breeding on lime plant and *Piper amalago* var. *amalago* plant. FIGS. 1 and 2 show images of gas chromatographs for lime plant and *Piper amalago* var. *amalago* plants, respectively. Tables 1A and 1B list the compositions of *Piper amalago* var. *amalago* plant oil and lime plant oil, respectively. Referring to FIG. 3, the chromatographs for *Piper amalago* var. *amalago* plant and lime plant superimposed revealed that a common oil, d-limonene, is found in both lime plant and *Piper amalago* var. *amalago* plant Therefore, extracts derived from lime plant and *Piper amalago* var. *amalago* plant make excellent chemical attractants.

TABLE 1A

Composition of *Piper amalago* var. *amalago* leaf oils by Gas Chromatography

| $T_R$/min | Compound[a] | % Area | RI[b] | ID[c] |
|---|---|---|---|---|
| 6.03 | α-pinene | 4.67 | 932 | GCMS, RI |
| 6.81 | β-pinene | 6.52 | 1026 | GCMS, RI |
| 7.27 | 3-carene | 9.42 | 1053 | GCMS, RI |
| 7.64 | 2,4-thujadiene | 19.99 | 1075 | GCMS, RI |
| 8.02 | d-limonene | 4.4 | 1097 | S/M, RI |
| 8.62 | (R,S) linalool | 5.93 | 1135 | GCMS, RI |
| 9.71 | camphor | 0.29 | 1208 | GCMS, RI |
| 10.19 | germacrene B | 2.64 | 1251 | GCMS, RI |
| 10.25 | α-terpineol | 1.75 | 1257 | GCMS, RI |
| 10.36 | crypton | 1.44 | 1267 | GCMS, RI |
| 11.18 | cuminaldehyde | 0.32 | 1352 | GCMS, RI |
| 11.66 | 4-(1-methylethyl)benzenemethanol | 0.36 | 1408 | GCMS, RI |
| 12.3 | piperitone | 0.48 | 1494 | GCMS, RI |
| 13.07 | α-cubene | 1.66 | 1610 | GCMS, RI |
| 13.19 | 1H-cyclopenta[1,3]cyclopropa[1,2]benzene | 0.78 | 1628 | GCMS, RI |
| 13.76 | caryophyllene | 0.87 | 1712 | GCMS, RI |
| 14.35 | γ-murolene | 1.04 | 1788 | GCMS, RI |
| 14.45 | α-gurjunene | 1.64 | 1801 | GCMS, RI |
| 14.5 | β-guaiene | 0.74 | 1807 | GCMS, RI |
| 14.64 | β-cadinene | 0.56 | 1824 | GCMS, RI |
| 14.71 | β-gurjunene | 2.94 | 1832 | GCMS, RI |
| 14.89 | α-cadinene | 1.84 | 1853 | GCMS, RI |
| 14.98 | calamenene | 4.01 | 1864 | GCMS, RI |
| 15.21 | nerolidol | 1.16 | 1891 | GCMS, RI |

TABLE 1A-continued

Composition of *Piper amalago* var. *amalago* leaf oils by Gas Chromatography

| $T_R$/min | Compound[a] | % Area | RI[b] | ID[c] |
|---|---|---|---|---|
| 15.79 | spathulenol | 1.23 | 1960 | GCMS, RI |
| 16.03 | caryophyllene oxide | 1.17 | 1988 | GCMS, RI |
| 16.33 | calarene | 1.64 | 2022 | GCMS, RI |
| 16.44 | α-guaiene | 0.78 | 2035 | GCMS, RI |
| 16.5 | copaene | 2.15 | 2042 | GCMS, RI |
| 16.66 | δ-selinene | 1.33 | 2060 | GCMS, RI |
| | Total | 83.75 | | |

[a]Elution order on HP capillary column.
[b]Retention index relative to n-alkane series($C_5$-$C_{30}$ excluding $C_{27}$ and $C_{29}$) on HP DB-5 column,
[c]GCMS identification by Gas-chromatography-Mass spectroscopy,
*matched by authentic internal standard

TABLE 1B

Composition of Lime Plant Essential Oils Obtained by Gas Chromatography

| $T_R$/min | Compound[a] | % Area | RI[b] | ID[c] |
|---|---|---|---|---|
| 4.47 | 4 hydroxy-4-methyl-2-pentanone | 10.13 | 994 | GCMS, RI |
| 6.92 | decane | 1.9 | 1002 | GCMS, RI |
| 7.59 | d-limonene | 22.04 | 1209 | GCMS, RI |
| 8.57 | undecane | 3.49 | 1095 | GCMS, RI |
| 9.54 | citronellal | 1.22 | 1484 | GCMS, RI |
| 9.93 | thujone | 1.92 | 1418 | GCMS, RI |
| 10.14 | dodecane | 0.54 | 1194 | GCMS, RI |
| 10.62 | nerol | 8.62 | 1752 | GCMS, RI |
| 10.93 | geraniol | 1.22 | 1797 | GCMS, RI |
| 11 | neral | 9.13 | 1701 | GCMS, RI |
| 11.40 | geranial | 12.91 | 1739 | GCMS, RI |
| 12.18 | geranyl acetate, (Z) | 2.9 | 1727 | GCMS, RI |
| 12.77 | geranyl acetate (E) | 2.74 | 1773 | GCMS, RI |
| 17.73 | squalene | 18.53 | 2633 | GCMS, RI |
| | Total | 97.28 | | |

[a]Elution order on HP capillary column.
[b] Retention index relative to n-alkane series($C_5$-$C_{30}$ excluding $C_{27}$ and $C_{29}$) on HP DB-5 column,
[c]GCMS identification by Gas-chromatography-Mass spectroscopy The amount and frequency for applying the chemical attractant to the host plant can be repeated as required to increase the percentage of the insect population that initially is attracted to the host plant species, or to induce residual insect populations to lay eggs on the host plant. Residual insect populations consist of mature target insects that prefer to feed and/or breed on plants other than that on which they were reared.

The chemical attractant is applied in an amount sufficient to induce target insects to feed or breed on the host plant. The amount sufficient to attract the target insects varies depending on the manner in which the chemical attractant is applied to the host plant and the type of host plant to which the chemical attractant is applied. Once applied, the chemical attractant lasts for about 12 to 24 hours or more, depending on the chemical stability and volatility of the chemical attractant and ambient conditions.

Further, the chemical attractant is applied to the host plant in an amount and a number of times sufficient to be recognized by target insect and be attractive to them. In one embodiment, the chemical attractant is applied to the host plant once per day. The chemical attractant can be applied to the host plant two, three, four, five, or more times per day. In another embodiment, the chemical attractant is applied to the host plant once per week. In other embodiments, the chemical attractant is applied to the host plant twice per day. In other embodiments the chemical attractant is applied to the host plant once, twice, three or more times per month. It can be applied before a rainfall, or after a rainfall. The chemical attractant can be applied when new leaves grow on the host plant. In another embodiment the chemical attractant is applied to the host plant when new leaves grow on the plant of interest.

The amount of chemical attractant used varies depending on the manner in which it is applied and the type of host plant to which it is applied. The amounts also vary depending on the species of target insect and ambient conditions. Using *Piper amalago* var. *amalago* plant oil in an alkane hydrocarbon aerosol mixture as an example, generally, the amount of *Piper amalago* var. *amalago* plant oil in the aerosol mixture required to induce a number of target insects to feed or breed on *Piper amalago* var. *amalago* plant instead of lime plant is about 0.01%-0.50% by weight. For example, the amount of *Piper amalago* var. *amalago* plant oil in the aerosol mixture is about 0.01%-0.05%; 0.05%-0.10%, 0.15%-0.20%; 0.20%-0.25%; 0.25%-0.30%; 0.30%-0.35%; 0.35%-0.40%; 0.40%-0.45%; or 0.45%-0.50% by weight.

In another aspect, the population size of target insects can be controlled by applying toxic extract to a plant of interest. Plants of interest naturally contain chemical attractant that induce target insects to breed on the plants of interest. However, toxic extracts derived from plants that may or may not also contain a chemical attractant or attractants, are poisonous to target insects and repel them. Therefore, in the embodiment in which toxic extracts are applied to the leaves of plants of interest, gravid female target insects are deterred from laying eggs or feeding on the treated plants. In another embodiment, toxic extracts are used as a pesticide and are applied directly to target insects. As a result, the majority of the offspring either die in early stages of the life cycle, or become deformed adults that are unable to fly and thus unable to reproduce and function normally. Thus, these methods thereby reduce the population size of, and protect plants of interest from being destroyed by feeding target insects.

In another embodiment, a kit useful for controlling insect egg laying or feeding on a plant is disclosed in which the kit contains toxic extract in an agriculturally acceptable carrier. Also included are instructions for applying the toxic extract to a plants of interest to repel target insects from laying eggs or feeding on treated plants of interest.

The toxic extract can be derived from a plant containing any toxin that repels, kills, or deforms target insects. For example, the toxic extract can be derived from *Piper aduncum, Piper hispidum, Piper fadyenii, Piper amalago* var. *amalago* plant, or it can be an isolated component such as apiol, which is a pesticidal compound found in *Piper aduncum* plant (see Table 1D).

In one embodiment of this aspect, toxic extract, derived from, for example, *Piper aduncum*, can be used to treat plants of interest to protect them from feeding and breeding *H. andraemon*. Treatment is considered effective when, e.g., a majority of target insects refuse to feed or breed on the plant to which the toxic extract is applied. In one or more embodiments, more than 50% of the target insects are deterred from feeding or breeding on the plant to which the extract is applied. In one or more embodiments, more than 55%, more than 60%, more than 65%, more than 70%, more than 75%, more than 80%, more than 85%, more than 90%, or more than 95% of the target insects are deterred from feeding or breeding on the plant to which the extract is applied.

In the aspect in which the toxic extract is applied to the plant of interest to repel target insects from feeding or breeding on plants of interest, it is applied in an amount and a number of times sufficient to be recognized by target insect and be deter them from feeding or breeding on the plant of interest. In the aspect in which the toxic extract is applied as a pesticide to eggs laid or larvae feeding on plants of interest, the toxic extract is applied in an amount and number of times sufficient to kill or deform target insects. In one embodiment of these aspects, the toxic extract is applied to the plant of interest once per day. In another embodiment, it is applied to the plant of interest two, three, four, five, or more times per day. In another embodiment, the toxic extract is applied to the plant of interest once per week. In other embodiments, the toxic extract is applied to the plant of interest twice per day. In other embodiments, the toxic extract is applied to the plant of interest once, twice, three or more times per month. It can be applied before a rainfall, or after a rainfall. The toxic extract can be applied when new leaves grow on the plant of interest. In another embodiment, the toxic extract is applied to the plant of interest when new leaves grow on the plant of interest.

The toxic extract is applied in an amount sufficient to deter target insects from feeding or breeding on the host plant to which the toxic extract is applied. The amount sufficient to deter the target insects varies depending on the manner in which it is applied to the host plant and the type of host plant. Once applied, the toxic extracts last for 12 to 24 hours, depending on ambient conditions and the volatility of the toxic extract. Application to plants of interest can be repeated as required to continue to deter target insects from feeding and laying eggs on treated plants.

The amount of toxic extract used varies depending on the manner in which it is applied and the type of plant of interest to which it is applied. The amounts also vary depending on the species of target insect and ambient conditions. Using *Piper aduncum* plant oil in an ethanol or water-based emulsion as an example, generally, the amount of *Piper aduncum* plant oil in the mixture required to repel the feeding and breeding of *H. andraemon* on plants of interest is about 0.1%-0.5%; 0.5%-1.0%, 1.0-1.5%, 1.5%-2.0%, 2.0%-2.5%, 2.5%-3.0%, 3.0%-3.5%, 3.5%-4.0%, 4.0%-4.5%, 4.5%-5.0%, 5.0%-5.5%, 5.5%-6.0%, 6.0%-6.5%, or 6.5%-7.0% by weight, preferably 5%. When used as a pesticide to kill or deform target insects on contact, the amount of *Piper aduncum* plant oil in the mixture required is about 0.1%-0.5%; 0.5%-1.0%, 1.0-1.5%, 1.5%-2.0%, 2.0%-2.5%, 2.5%-3.0%, 3.0%-3.5%, 3.5%-4.0%, 4.0%-4.5%, 4.5%-5.0%, 5.0%-5.5%, 5.5%-6.0%, 6.0%-6.5%, or 6.5%-7.0% by weight, preferably 2%.

Table 1C shows the chemical composition of the oil derived from *Piper amalago* var. *nigrinodum* plant. *H. andraemon* is not known to feed on *Piper amalago* var. *nigrinodum* plant in the wild. This is consistent with the observed unsuitability of *Piper amalago* var. *nigrinodum* plant to be a host plant for *H. andraemon*, and is further confirmation that d-limonene is a chemical attractant for *H. andraemon*. The oil recovered is very pale yellow to colorless with an odor similar to that of black pepper. The leaves or extract from *Piper amalago* var. *nigrinodum* plant, as shown in Table 1C, do not contain the attractant d-limonene.

As shown in Table 1D, the oil derived from *Piper aduncum* plant also does not contain the attractant d-limonene, but does contain a significant amount of the oil of the pesticide apiol (71.06%), which makes *Piper aduncum* as excellent deterrent. *H. andraemon* is not known to feed on this species of plant in the wild.

TABLE 1C

Composition of *Piper amalago* var. *nigrinodum* Plant Essential Oils Obtained by Gas Chromatography

| $T_R$/min | Compound[a] | % Area | RI[b] | ID[c] |
|---|---|---|---|---|
| 4.46 | heptane | 10.6 | 700 | GCMS, RI |
| 10.95 | α-pinene | 10.95 | 1032 | GCMS, RI |
| 6.31 | camphene | 1.77 | 1076 | GCMS, RI |
| 6.64 | sabinene | 10.42 | 1158 | GCMS, RI |
| 6.81 | β-pinene | 11.02 | 1124 | GCMS, RI |
| 7.28 | 3-carene, | 1.71 | 1130 | GCMS, RI |
| 7.62 | β-phellandrene | 16.25 | 1279 | GCMS, RI |
| 8.61 | (R,S) linalool | 2.66 | 1151 | GCMS, RI |
| 10.25 | α-terpineol | 1.62 | 1688 | GCMS, RI |
| 10.36 | crypton | 1.8 | 1124 | GCMS, RI |
| 11.17 | 4-(1-methylethyl)benzenaldehyde | 0.46 | 1789 | GCMS, RI |
| 11.65 | 4-(1-methylethyl) benzenemethanol | 0.29 | 1517 | GCMS, RI |
| 11.69 | bornyl acetate | 0.66 | 1560 | GCMS, RI |
| 12.55 | (+)-2-carene | 0.35 | 1110 | GCMS, RI |
| 13.07 | copaene, | 0.48 | 1376 | GCMS, RI |
| 13.77 | caryophyllene | 1.12 | 1707 | GCMS, RI |
| 14.01 | valencene | 0.51 | 1714 | GCMS, RI |
| 14.98 | calamenene | 1.23 | 1875 | GCMS, RI |
| 15.21 | trans -nerolidol | 1.77 | 2058 | GCMS, RI |
| 15.79 | spathulenol, | 2.56 | 2126 | GCMS, RI |
| 16.03 | caryophyllene oxide | 1.51 | 1973 | GCMS, RI |
| 17.18 | β-gurjunene | 7 | 1611 | GCMS, RI |
| 17.27 | α-guaiene | 9.94 | 1657 | GCMS, RI |
| | Total | 96.68 | | |

[a] Elution order on HP capillary column.
[b] Retention index relative to n-alkane series($C_5$-$C_{30}$ excluding $C_{27}$ and $C_{29}$) on HP DB-5 column,
[c] GCMS identification by Gas-chromatography-Mass spectroscopy

TABLE 1D

Composition of *Pipe aduncum* Leaf Essential Oils Obtained by Gas Chromatography

| | Compound[a] | Retention time | RI | Area |
|---|---|---|---|---|
| 1 | α-pinene | 6.71 | 953 | 0.31 |
| 2 | β-pinene | 7.5 | 979 | 0.34 |
| 3 | β-myrcene | 7.66 | 988 | 0.14 |
| 4 | m-cymene | 8.3 | 1026 | 0.87 |
| 5 | trans-β-ocimene | 8.46 | 1035 | 1.98 |
| 6 | cis-β-ocimene | 8.64 | 1046 | 2.97 |
| 7 | 3-carene | 8.87 | 1060 | 0.54 |
| 8 | α-terpinolene | 9.32 | 1087 | 0.22 |
| 9 | terpinen-4-ol | 10.92 | 1182 | 1.61 |
| 10 | d-piperitone | 12.27 | 1260 | 3.96 |
| 11 | copaene | 14.27 | 1382 | 0.42 |
| 12 | germacrene A | 14.45 | 1394 | 0.26 |
| 13 | caryophyllene | 14.97 | 1430 | 1.68 |
| 14 | α-caryophyllene | 15.48 | 1466 | 0.65 |
| 15 | β-cubene | 15.83 | 1490 | 1.30 |
| 16 | myristicin | 16.31 | 1526 | 3.53 |
| 17 | elemicin, (Z) | 16.59 | 1547 | 0.41 |
| 18 | nerolidol | 16.77 | 1561 | 0.28 |
| 19 | γ-elemene | 16.9 | 1572 | 0.23 |
| 20 | (−)-spathulenol | 17.11 | 1588 | 0.23 |
| 21 | caryophyllene oxide | 17.2 | 1595 | 0.86 |
| 22 | γ-selinene | 17.35 | 1607 | 0.79 |
| 23 | apiol | 17.65 | 1632 | 71.06 |
| 24 | 4,5-dihydro-1,3-diphenyl-1H-pyrazole, | 17.77 | 1642 | 0.37 |
| 25 | calarene | 17.92 | 1655 | 0.55 |
| | Total | | | 95.56 |

[a] Elution order on HP capillary column.
[b] Retention index relative to n-alkane series($C_5$-$C_{30}$ excluding $C_{27}$ and $C_{29}$) on HP DB-5 column,
[c] GCMS identification by Gas-chromatography-Mass spectroscopy Chemical attractants can be comprised of one of several chemicals. In one embodiment, the chemical attractant is derived from host plants, which contain attractants and toxins. In another embodiment, the chemical attractant is derived from plants of interest that contain attractants but not toxins. The chemical attractant can be an extract of soluble components from either the host plant or plant of interest.

Similarly, toxic extracts can be comprised of one of several chemicals. In one embodiment, the toxic extract is derived from plants that contain toxins. In another embodiment, the toxic extract is derived from host plant, which contain, in addition to chemical attractant, toxins that repel target insects. Further, the toxic extract can be an extract of soluble components from a host plant, or other type of plant that contains a chemical that repels target insects.

Chemical attractants and toxic extracts can contain components soluble in hydrophobic medium as an oil extract or in hydrophilic and aqueous media as a water extract. Extracts can be obtained using techniques known in the art, such as hydrodistillation, hydro diffusion, cold pressing, extraction using a hydrocarbon solvent, super critical fluid extraction using carbon dioxide and other super critical fluids, steam distillation, fractional distillation, enfleurage extraction, maceration extraction, including those processes with zeolite removal of the water after maceration, and spinning cone extraction. Isolation and purification of individual or groups of chemical compounds can be accomplished using methods established in the art, such as gas, liquid, including such developments as high performance liquid chromatography (HPLC), high performance liquid chromatography guided by mass spectroscopy (HPLC-MS), high performance liquid chromatography guided by nuclear magnetic resonance spectroscopy (HPLC-NMR), multiple high performance liquid chromatography (HPLC-HPLC), ultra-performance liquid chromatography (UPLC), and ultra-performance liquid chromatography coupled to-time-of flight mass spectrometry (UPLC-TOF-MS), countercurrent or centrifugal partition chromatography (CCC or CPC), column, and size-exclusion chromatography, homogenization, distillation, and fractional distillation.

Chemical attractant and toxic extract can be applied to plants, and in the case of toxic extract, directly to target insects, in the form of a spray, paste, gum, oil, solution, aerosol, mist, dust, fume, and/or gas. Chemical attractant is applied in an amount sufficient to affect the egg-laying behavior of target insects. The egg-laying behavior is affected in that the plant on which the target insect prefers to feed or breed changes from the plant of interest (its food source and preferred place for egg laying under natural conditions) to the particular type of host plant on which the target insect was reared. The chemical attractant can be in the form of an aerosol, where the aerosol is a mixture of butane, propane, and the chemical attractant, and can be applied by spray or mist. Toxic extract is applied in an amount sufficient to deter target insects from feeding or breeding in treated plants of interest. Toxic extract can be in the form of an emulsion with water and a suitable alcohol, such as ethanol.

Species of plant were collected and deposited in the Herbarium in the Department of Life Sciences at the University of West Indies, Mona, Jamaica. For identification purposes, the plants used in these methods were assigned the following accession numbers:

| Plants | Accession Numbers |
|---|---|
| *Citrus aurantifolia* | 35266 |
| *Citrus sinensis* | 35267 |
| *Piper amalago* var. *amalago* | 35268 |
| *Piper amalago* var. *nigrinodum* | 35291 |
| *Zanthoxylum martinicense* | 35289 |
| *Piper aduncum* | 35435 |

EXAMPLES

Example 1

To rear *H. andraemon* larvae on citrus plants and *Piper amalago* var. *amalago* plants, 77 larvae were laid on various citrus plant species, including lime plant, *Citrus sinensis* (sweet orange), and *Citrus reticulata* (Mandarin orange). The larvae were then manually removed and reared on *Piper amalago* var. *amalago* plants. The larvae were transferred at different stages, but early in their life cycles (first, second, or third instars). Measurements of the widths of the broadest part of the pupae were measured, and time to pupation was taken to determine host plant suitability. The larvae were placed in a cage of about 3 meters by 3 meters by 2.5 meters and were exposed to normal ambient environmental conditions. Statistical analysis was used to determine whether there were significant differences between the size of the larvae bred on *Piper amalago* var. *amalago* plant and citrus plants.

Time to pupation was determined by noting the time taken for larvae to pupate after hatching for both lime plant and *Piper amalago* var. *amalago* plant-reared larvae. The leaves of both plants on which the eggs were laid were removed from the cage and replaced with fresh leaves. The number of pupae and number of days the larvae took to pupate was recorded. Statistical analysis was used to determine whether there were significant differences between the times it took larvae bred on lime plant and larvae bred on *Piper amalago* var. *amalago* plant to pupate.

Various measurements were taken to compare the suitability of *Piper amalago* var. *amalago* plant as a host-plant substitute for citrus plants. Once mature, the feeding and breeding behavior of *Piper amalago* var. *amalago* plant-reared butterflies was compared to lime plant-reared butterflies. The experiments and the results, which demonstrated that the feeding and breeding behavior of butterflies can effectively be controlled with the use of chemical attractants, are summarized in the Examples 2-8.

Example 2

Fresh whole leaves of lime plant and *Piper amalago* var. *amalago* plant were used to extract oil for application to host plants. The leaves were then hydrodistilled for up to 4 hours using a Clevenger-type apparatus. The oils were collected during distillation at one hour intervals, and were dried over anhydrous sodium sulfate to yield substantially clear oils. Extractions were done in triplicate and the average values were used. The oils were weighed and stored at 5° C.

Hydrodistilling 952.7 g of lime plant yielded 1.44 g of oil, 0.151% by weight; 378.6 g of *Piper* plant yielded 0.446 g of oil, 0.085% by weight; 193.2 g *Citrus sinensis* leaves yielded 0.782 g of oil, 0.405% by weight; 794 g of *P. amalago*, var. *nigrinodum* leaves yielded 0.719 g of oil, 0.091% by weight; and 207.9 g of *Zanthoxylum martinicense* leaves yielded 0.0365 g of oil, 0.0176% by weight.

A Varian CP-3800 gas chromatograph interfaced with a Flame ionization detector (FID) was used to analyze the extracted oils. The gas chromatograph was equipped with a WCOT fused silica coated with CP WAX 52CB capillary column (length 60 m×inner diameters 0.25 mm; 0.25 μm film thickness). The carrier gas was Nitrogen, at a flow rate of 1 mL min$^{-1}$, split 1:100. The injector temperature was 250° C. The column oven temperature of 40° C. was held for 1 minute, then increased from 40° C. to 100° C., at a rate of 10° C. min$^{-1}$ held for 1 minute, then increased from 100° C. to 200° C. at a rate of 20° C. min$^{-1}$, held for 1 minute, and finally increased from 200° C. to 250° C. at a rate of 10° C. min$^{-1}$, and held for 25 minutes. The FID temperature was maintained at 300° C.

The retention indices (RI) were calculated using a mixture of homologous series of n-alkanes $C_8$-$C_{25}$ analyzed under the same conditions as each oil sample (GC-FID analysis). RI values were calculated using Kovats' procedure for temperature programming GC equations. (IUPAC. Compendium of Chemical Terminology, Kovats (Retention) Index; 1997).

The chemical compositions of the oils were also determined using GC-MS using a Hewlett Packard (HP) 6890 system Gas Chromatograph interfaced with a HP-5973 Mass Spectrometer. The gas chromatograph was equipped with a DB-VRX fused silica column (length 20 m×internal diameters 0.18 mm, film thickness of 1 μm). Analytical conditions employed were Helium for a carrier gas at a flow rate of 1 mL min$^{-1}$, split less mode, with an injector temperature of 250° C., interface temperature of 280° C. The temperature program was the same used for the GC-FID analyses previously described. The mass spectra data were collected with ionization energy of 70 eV and a mass range of 50-500 M/Z. An n-alkane mixture was also analyzed under the same temperature program and other conditions, and the Retention Indices (RI) calculated for each compound.

The components in the oils were matched with mass spectral data of the NIST 98 library. Peaks that had a peak quality match greater than 70% were considered matches with the compound from the library. Peaks of substantial quantity but poor quality were identified either by matching gas chromatography analyses with authentic compounds run in several programs, or by a comparison of the retention indices against the published data in Adams. (Adams, Robert, Identification of oil components by gas chromatography/ quadruple mass spectrometry; 2001: 9-40). The presence of d-limonene in *Piper amalago* var. *amalago* leaf oil was confirmed by matching against authentic d-limonene in several temperature programs: the standard program mentioned previously, and two additional temperature programs, firstly, heated initially to 40° C. and held at this temperature for 3 min., then heated from 40° C. to 80° C. at a rate of 5° C. min$^{-1}$, and held at this temperature for 1 min., then heated from 80° C. to 200° C. at a rate of 10° C. min$^{-1}$, and held at this temperature for 2 min., then finally heated from 200° C. to 250° C. at a rate of 10° C. min$^{-1}$, and held at 250° C. for 10 min., and secondly, heated initially to 40° C. and held at this temperature for 3 min., then heated from 40° C. to 120° C. at a rate of 10° C. min$^{-1}$ and held at 120° C. for 3 min., then heated from 120° C. to 180° C. at a rate of 20° C. min$^{-1}$ held at that temperature for 5 min., then finally heated from 180° C. to 250° C. at a rate of 20° C. min$^{-1}$, and held at that temperature for 1 min.

Fresh leaves were collected to extract the oils for analysis by gas chromatography. The leaves were weighed and hydrodistilled for up to four hours, using a Clevenger type apparatus. The extractions were done in triplicate and the essential oils were collected during distillation at hourly intervals. The oils obtained were then dried over anhydrous sodium sulfate and yielded clean, clear oils. The oils were then weighed and stored at 5° C., in a refrigerator for further analysis.

The aerosol mixture for application to citrus plant and *Piper amalago* var. *amalago* plant materials was prepared by combining lime plant oil, *Piper amalago* var. *amalago* plant oil, d-limonene, or a combination thereof, with an alkane hydrocarbon mixture consisting of 28% butane and 72% propane. The aerosol was filled to a concentration of, e.g., 0.25% by weight of *Piper amalago* var. *amalago* plant oil in the hydrocarbon mixture or, e.g., 0.45% by weight of lime plant oil in the hydrocarbon mixture.

Example 3

To determine the suitability of *Piper amalago* var. *amalago* plant as a host plant, the size of larvae were compared after feeding on either *Piper amalago* var. *amalago* plant or lime plant. In this experiment, larvae were reared on *Piper amalago* var. *amalago* plant or lime plant to compare the size of the larvae after they fed on one of either plant.

TABLE 2

Comparison of pupae size (mm)

|  | Pupae bred on *Piper amalago* var. *amalago* plant | Pupae bred on citrus plant |
|---|---|---|
| Population size: | 77 | 72 |
| Mean width: | 8.710 mm. | 8.853 mm. |
| Standard Deviation: | 1.0354 | 1.0978 |

The results, reflected in Table 2, show that the difference in the mean widths of pupae bred on *Piper* plant and lime plant was minimal at about 0.1 mm. The Levene's test for equality of variance indicated that the variance in size were not significantly different (p=0.432). Because no significant difference was found between the size of pupae bred on *Piper amalago* var. *amalago* plant versus lime plant, *Piper amalago* var. *amalago* plant was determined to be a suitable host plant substitute for lime plant.

Example 4

The sex ratios of the larvae were compared to determine the suitability of *Piper amalago* var. *amalago* plant as a host-plant substitute for lime plant. To determine the sex ratios of butterflies bred on lime plant and *Piper amalago* var. *amalago* plant, a random population of 45 lime plant and 39 *Piper amalago* var. *amalago* plant-reared butterflies was selected. The butterflies were reared to adulthood on either lime plant or *Piper amalago* var. *amalago* plant.

TABLE 3

Comparison of sex ratios of *H. andraemon* larvae bred on *Piper amalago* var. *amalago* plant and citrus plant

|  | Male | Female | Totals |
|---|---|---|---|
| Observed citrus-plant reared: | 24 | 21 | 45 |
| Observed *Piper*-plant reared: | 17 | 22 | 39 |
| Totals | 41 | 43 | 84 |

TABLE 3A

Chi-squared values observed, and expected number of male and female butterflies from citrus-reared larvae

|  | Male | Female | Totals |
|---|---|---|---|
| Observed (O) | 24 | 21 | 45 |
| Expected (E) | 22.5 | 22.5 | 45 |
| $\chi^2$ | 0.1977 | Yates Corrected value | 0.0889 |

TABLE 3B

Chi-squared values observed, and expected number of male and female butterflies from *P. amalago* var. *amalago* -reared larvae

|  | Male | Female | Totals |
|---|---|---|---|
| Observed (O) | 17 | 22 | 39 |
| Expected (E) | 19.5 | 19.5 | 39 |
| $\chi^2$ | 0.641 | Yates Corrected value | 0.410 |

TABLE 3C

Sex ratios for *Piper amalago* var. *amalago* plant-reared and citrus-plant reared larvae

|  | Male | Female | Totals |
|---|---|---|---|
| citrus plant reared: | 24 | 21 | 45 |
| *Piper amalago* var. *amalago* plant reared: | 17 | 22 | 39 |
| Totals | 41 | 43 | 84 |

TABLE 3D

Calculated data for chi-squared contingency test on sex ratios for *Piper amalago* var. *amalago* plant-reared and citrus-reared larvae

|  | Male | Female | Totals |
|---|---|---|---|
| Observed citrus plant reared (O) | 24 | 21 | 45 |
| Expected (E) | 21.96 | 23.04 | 45 |
| Observed *Piper amalago* var. *amalago* plant reared (O) | 17 | 22 | 39 |
| Expected (E) | 19.04 | 19.96 | 39 |
| $\chi^2$ | 0.796 |  |  |

After the emergence of the adult butterfly, sex was determined by viewing the pupal shell under a light microscope at 10× magnification. The shells were noted as either male or female based on the appearance of two spots in either the first or second segment, according to the method by George Warenecke, The Young Specialist Looks at Butterflies and Moths; 1964: 34-35.

The values were assigned a chi square value of 0.796 compared to the P value at 0.001 of 10.10.83 (Table 3D). The calculated chi squared values were less than the tabulated values (p>0.001), which were in agreement that the observed data does not differ significantly from the expected data. Variation in the sex ratios was attributed to chance, and the number of male and female butterflies obtained from each host plant was in accordance with that which is expected from natural selection, for a sex ratio of 1:1.

The results of this experiment indicate that *Piper amalago* var. *amalago* plant is a suitable host-plant substitute for lime plant.

Example 5

The suitability of *Piper amalago* var. *amalago* plant as a host plant was further experimented by comparing life cycles of *H. andraemon* bred on *Piper amalago* var. *amalago* plant to those bred on lime plant. The life cycles of *H. andraemon* bred on *Piper amalago* var. *amalago* plant and *H. andraemon* bred on lime plant were very similar. The days from hatching to pupation were about 17 to 23 days, and the emergence of the adult from the pupa was about 10 days to 3 weeks.

Example 6

To further evaluate the suitability of *Piper amalago* var. *amalago* plant to serve as a host plant in place of naturally preferred citrus plant, the number of offspring yielded from egg laying on *Piper amalago* var. *amalago* plant was compared to that from citrus plants.

TABLE 4

Number of eggs laid on *Piper amalago* var. *amalago* plant and citrus plant by *H. andraemon* reared on *Piper amalago* var. *amalago* and citrus plants

| Plant on which Butterflies were reared | Number of eggs laid on citrus plant | Number of eggs laid on *Piper amalago* var. *amalago* plant | Total |
|---|---|---|---|
| Larvae reared on citrus plant (%) | 64 (89%) | 8 (11%) | 72 (100%) |
| Larvae reared on *Piper amalago* var. *amalago* (%) | 2 (4%) | 53 (96%) | 55 (100%) |
| Total no. of eggs | 66 | 61 | 127 |

TABLE 4A

Number of eggs laid by *Piper amalago* var. *amalago* plant-reared butterflies on individual host plants

| Total eggs laid | Number of eggs laid on *Piper amalago* var. *amalago* plant | Number of eggs laid on citrus plant |
|---|---|---|
| 55 | 53 | 2 |
| Percentage of total eggs laid | 96% | 4% |

TABLE 4B

Number of eggs laid by citrus-plant bred butterflies on individual host plants

| Total eggs laid | Number of eggs laid on *Piper amalago* var. *amalago* plant | Number of eggs laid on citrus plant |
|---|---|---|
| 72 | 8 | 64 |
| Percentage of total eggs laid | 11% | 89% |

TABLE 4C

Observed and expected number of eggs laid on each host plant by *H. andraemon*

| | Number of eggs laid on citrus plant | Number of eggs laid on *Piper amalago* var. *amalago* plant | Total |
|---|---|---|---|
| Larvae reared on citrus plant | 64 * (37.417) | 8 * (34.583) | 72 |
| Larvae reared on *Piper amalago* var. *amalago* | 2 * (28.583) | 53 * (26.417) | 55 |
| Total | 66 | 61 | 127 |

* values in brackets are calculated expected values
Calculated chi-square value = 90.79, P at 0.001 at 1 degree of freedom = 10.83.

Table 4 shows the startling result that gravid females lay eggs on the same species of host plant on which they were reared. In this example, *Piper amalago* var. *amalago* plant-bred butterflies were allowed to choose between laying eggs on *Piper amalago* var. *amalago* plant and lime plant. The plants were arranged in varying directions to avoid selection based on orientation. A chi-squared contingency test on the relationship between the plant species of rearing and the plant species of egg-laying gave a highly significant result, ($X^2$=90.79 at 1 degree of freedom, giving a value of p<0.001), indicating that the species that the butterflies are reared on, does influence the species on which they prefer to lay their eggs.

Referring to Table 4A, in a population of 55 eggs laid by *Piper amalago* var. *amalago* plant-bred butterflies, when given the choice of laying eggs on *Piper amalago* var. *amalago* plant or lime plant, 53 eggs, or 96%, were laid on *Piper amalago* var. *amalago* plant, and only 2 eggs, or 4%, were laid on lime plant. Similarly, lime plant-reared butterflies were given the choice of laying eggs on *Piper amalago* var. *amalago* and lime plants. Table 4B shows that 64 eggs, or 89%, were laid on lime plant by lime plant-reared butterflies, and only 8 eggs, or 11%, were laid on *Piper amalago* var. *amalago* plant.

Table 4C shows that the calculated chi square value was 90.79, which was greater than the tabulated value of 10.83 at P=0.001. The eggs laid on the host plant other than the species on which the larvae were themselves reared were attributed to chance.

These results show that the butterflies overwhelmingly preferred to rear their offspring on the same type of plant on which they were reared. Therefore, butterflies initially induced by a chemical attractant to lay eggs on *Piper amalago* var. *amalago* plant instead of citrus plant yield offspring that also prefer that species of plant.

Example 7

The faithfulness of egg laying of lime plant-bred butterflies on lime plant versus *Piper amalago* var. *amalago* plant was compared to further determine the suitability of *Piper amalago* var. *amalago* plant as a lime plant substitute for controlling feeding and egg laying behaviors of butterflies.

*H. andraemon* larvae were reared on lime plant. When they pupated and were ready to lay eggs, they were given the choice of plants on which to lay eggs: unsprayed lime plants, unsprayed *Piper amalago* var. *amalago* plants, *Piper amalago* var. *amalago* plants sprayed with lime plant oil, and *Piper amalago* var. *amalago* plants sprayed with d-limonene. Egg laying was permitted to continue until the butterflies ceased laying eggs. Nearly 100% of the eggs laid hatched into larvae.

Table 5 summarizes the results of an experiment in which the faithfulness of egg laying on the species of plant on which the butterflies were reared was confirmed. In this experiment, both lime plant oil and d-limonene were sprayed onto *Piper amalago* var. *amalago* plant to determine whether the butterflies discriminated between the two.

TABLE 5

Egg laying of citrus-plant bred *H. andraemon* given a choice of plants on which to lay

| | Plants | No. of eggs laid | % |
|---|---|---|---|
| a. | Unsprayed lime plant | 93 | 44.71 |
| b. | Unsprayed *Piper amalago* var. *amalago* | 11 | 5.29 |
| c. | *Piper amalago* var. *amalago* sprayed with lime plant oil | 52 | 25.00 |
| d. | *Piper amalago* var. *amalago* sprayed with d-limonene | 52 | 25.00 |
| | Totals | 208 | 100.00 |

As expected, most of the eggs were laid on unsprayed lime plants, confirming that lime plant-reared butterflies preferentially re-lay eggs on lime plants. Only 5.29% of eggs were laid on unsprayed *Piper amalago* var. *amalago* plants. The surprising result, which is not naturally occurring, was that gravid females perceived *Piper amalago* var. *amalago* plants sprayed with either lime plant oil or d-limonene similarly, as reflected by the 52 eggs laid on *Piper amalago* var. *amalago* plants sprayed with lime plant oil and the 52 eggs laid on *Piper amalago* var. *amalago* plants sprayed with d-limonene. Moreover, these results show that sprayed *Piper amalago* var. *amalago* plants, on which 50% of eggs were laid, were perceived similar to unsprayed lime plants, and are therefore suitable for inducing egg laying on species other than citrus plant.

Example 8

The faithfulness of egg laying of *Piper amalago* var. *amalago* plant-bred butterflies on *Piper amalago* var. *amalago* plant versus lime plant was compared to further determine the suitability of *Piper amalago* var. *amalago* plant as a lime plant substitute for controlling feeding and egg laying behaviors of butterflies.

*H. andraemon* larvae were reared on *Piper amalago* var. *amalago* plant. When they pupated and were ready to lay eggs, the butterflies were given the choice of plants on which to lay eggs: unsprayed lime plants, unsprayed *Piper amalago* var. *amalago* plants, citrus plant sprayed with *Piper amalago* var. *amalago* plant oil, and citrus plant sprayed with d-limonene. The egg laying was permitted to continue until the butterflies ceased laying eggs. Nearly 100% of the eggs laid hatched into larvae.

TABLE 6

Egg laying of *Piper amalago* var. *amalago* plant bred *H. andraemon* given a choice of plants on which to lay

| | Plants | No. of eggs laid | % |
|---|---|---|---|
| a. | Unsprayed *Piper amalago* var. *amalago* plant | 133 | 68.91 |
| b. | Unsprayed lime plant | 8 | 4.15 |
| c. | Citrus plant sprayed with *Piper amalago* var. *amalago* plant oil | 26 | 13.47 |
| d. | Citrus plant sprayed with d-limonene | 26 | 13.47 |
| | Totals | 193 | 100.00 |

Table 6 summarizes the results of the experiment in which *Piper amalago* var. *amalago* plant bred butterflies were given the choice of plants on which to lay eggs. 68.91% of the eggs were laid on *Piper amalago* var. *amalago* plant, establishing that *Piper amalago* var. *amalago* plant reared butterflies prefer to breed on the type of plant on which they were reared. As expected, few eggs, or 4.15%, were laid on unsprayed lime plant. In total, *Piper amalago* var. *amalago* plant reared butterflies re-laid eggs on *Piper amalago* var. *amalago* plants about 96% of the time and on unsprayed lime plant only about 4% of the time.

This experiment confirmed that butterflies reared on *Piper amalago* var. *amalago* plant preferred to lay eggs on *Piper amalago* var. *amalago* plant when given a choice between sprayed and unsprayed *Piper amalago* var. *amalago* plant and both sprayed and unsprayed lime plant. Thus, the use of chemical attractants to induce butterfly egg laying on, e.g., *Piper amalago* var. *amalago* plant instead of commercially valuable plants such as citrus plants, is an effective method for controlling the feeding and breeding of butterflies.

Example 9

Butterflies were induced to lay on host plant *Piper aduncum* plant sprayed with lime plant oil, or lime plant sprayed with *Piper aduncum* plant oil. *Piper aduncum* shoots were collected in Andrew, Jamaica, and 297.35 g of leaves were placed in a Clevenger-type extractor and extracted with boiling water. Once extracted according to the methods described in Example 2, 0.8919 g of a clear oil with a minty-like odor was obtained, a yield of 0.30% by weight.

Four *Heraclides andraemon* pupae were placed in the cage previously described in Example 1. Three pupae hatched into adults, two males and a female, which were allowed to mate and lay eggs. They were given a choice of four types of plants on which to lay: unsprayed *Piper aduncum* cuttings; *Piper aduncum* cuttings sprayed with d-limonene; unsprayed lime seedlings; and lime seedlings sprayed with the *Piper aduncum* emulsion. These plants, all with young leaves, were placed around the cage.

Cuttings from the *Piper aduncum* shoots with young leaves were used to attempt to induce butterflies to feed and lay eggs on a *Piper aduncum* plant treated with lime plant extract. The *Piper aduncum* cuttings were sprayed twice daily for eight days, once in the morning and once in the afternoon, with a d-limonene aerosol formulation. The d-limonene aerosol formulation was prepared as a hydrocarbon mixture of 72% propane and 28% butane, with 0.15% d-limonene.

Lime plant seedlings were sprayed with a 5% *Piper aduncum* emulsion twice daily for eight days, except no spraying occurred on day five.

As shown in Table 7, the butterflies preferred to lay eggs on unsprayed lime plant seedlings, and did not lay any eggs on unsprayed *P. aduncum* cuttings or *Piper aduncum* cuttings sprayed with d-limonene.

After day five, the period during which no *Piper aduncum* emulsion was sprayed on the lime seedlings, the butterflies, for the first time, took an interest in the lime seedlings that had previously been sprayed with the *Piper aduncum* leaf oil. We observed 9 eggs laid on the young shoots of these lime seedlings that had previously been sprayed with *Piper aduncum* emulsion. After spraying resumed on day 6, however, the butterflies again took no interest in the lime seedlings sprayed with *Piper aduncum* emulsion.

TABLE 7

*H. andraemon* egg laying on lime plant seedling and *P. aduncum*

| Plant | No. of Eggs after 5 Days | No. of Eggs after 8 Days | % |
|---|---|---|---|
| Unsprayed *P. aduncum* cuttings | 0 | 0 | 0% |
| *P. aduncum* cuttings sprayed with d-limonene | 0 | 0 | 0% |
| Unsprayed lime seedlings | 64 | 79 | 88.8% |
| Lime seedlings sprayed with *P. aduncum* oil. | 9 | 9 | 11.1% |
| Totals | 73 | 88 | 100% |

Example 10

To determine the toxicity of *Piper aduncum* leaf essential oil, eighty second instar *H. andraemon* larvae were sprayed daily with 2 mL of 2% solution of *Piper aduncum* leaf essential oils in ethanol with a Potter's tower. For the control, 13 second instar *H. andraemon* larvae were sprayed daily with 2 mL of ethanol with a Potter's tower.

Seventy-eight of the larvae sprayed with *Piper aduncum* leaf essential oils and ethanol died before pupation (97.5% mortality). Two surviving larvae, both males, pupated after an abnormally lengthy period, 25 days. The two surviving males emerged from pupation after 14 and 16 days respectively. Both appeared normal and were able to fly, mate, and lay.

In the control experiment, all 13 larvae pupated after 17 days. They appeared normal, except that two had one wing that was slightly smaller than the other. All 13 adults, however, were able to fly, mate, and lay.

It is to be understood that while the invention has been described in conjunction with the detailed description thereof, the foregoing description is intended to illustrate and not limit the scope of the inventions, which are defined by the scope of the appended claims. Other aspects, advantages, and modifications are within the scope of the following claims.

What is claimed is:

1. A method of controlling the population size of a citrus-feeding swallowtail butterfly (*Heraclides andraemon*) species which naturally feeds on a plant of interest, comprising:
    (a) providing a host plant in a pretreatment state and selecting a chemical attractant extracted from the plant of interest which naturally attract the citrus-feeding swallowtail butterfly (*Heraclides andraemon*) species;
    (b) applying to the host plant the chemical attractant to attract the citrus-feeding swallowtail butterfly (*Heraclides andraemon*) species to the host plant and to cause the citrus-feeding swallowtail butterfly (*Heraclides andraemon*) species to lay eggs on the host plant and an extract from Piper plant that contains a toxin that kills the citrus-feeding swallowtail butterfly (*Heraclides andraemon*) species;
    wherein a majority of the citrus-feeding swallowtail butterfly (*Heraclides andraemon*) species or the laid eggs die from ingesting the extract or coming into contact with the extract.

2. The method of claim 1, wherein the chemical attractant is detectable by the swallowtail butterfly species.

3. The method of claim 1, wherein application of the mixture consists of dipping, spraying, coating, diluting, covering, saturating, misting, fumigating, or dusting the host plant with the mixture.

4. The method of claim 1, wherein the swallowtail butterfly species is selected from a group consisting of *Heraclides* (syn. *Papilio*) *andraemon* Hubner, *Heraclides andraemon: bonhotei* Sharpe, *Heraclides andraemon: andraemon* Hubner, *Heraclides andraemon: hernandezi* de la Torre, *Heraclides andraemon: tailori* Rothschild, and *Heraclides andraemon: tailori* Jordan.

5. The method of claim 1, wherein the host plant is a plant on which the swallowtail butterfly species naturally feeds in the wild.

6. The method of claim 1, wherein the host plant is a citrus plant.

7. The method of claim 1, wherein the host plant is a Piper plant that contains limonene or d-limonene.

8. The method of claim 1, wherein the host plant is one or more plants selected from the group consisting of *Citrus aurantifolia* (Christm.) Swingle (Rutaceae), *Piper amalago* var. *amalago* L. (Piperaceae), lime, *C. limon* (L.) Burm. F., lemon, *C. sinensis* (L.) Osbeck, sweet orange, *C. reticulata* Blanco, Mandarin orange, tangerine, *C. paradisi* Macf, grapefruit, *C. medica* L., citron, *C. aurantium* L. Seville orange, *C. grandis* (L.) Osbeck, shaddock, pummelo, *C. maxima* (Burm.) Merr, ugli, *C. reticulata* Blanco x *C. sinensis* (L.) Osbeck, ortanique, *C. mitis* Blanco, calamondin, *Fortunella margarita* Lour. Swingle, kumquat (Rutaceae), *Amyris* P. Browne Rutaceae), *Zanthoxylum* L., *Zanthoxylum martinicense* (Lam.), *Lantana camara, Jatropha podagrica, Canna indica*, and *Z. pterota* L. (Rutaceae).

9. The method of claim 1, wherein the chemical attractant comprises oil derived from a host plant that contains limonene or d-limonene.

10. The method of claim 1, wherein the chemical attractant comprises oil derived from a citrus plant.

11. The method of claim 1, wherein the chemical attractant comprises oil derived from one or more plants selected from the group consisting of *Citrus aurantifolia* (Christm.), Swingle (Rutaceae), *Piper amalago* var. *amalago* L. (Piperaceae), lime, *C. limon* (L.) Burm. F., lemon, *C. sinensis* (L.) Osbeck, sweet orange, *C. reticulata* Blanco, Mandarin orange, tangerine, *C. paradisi* Macf, grapefruit, *C. medica* L., citron, *C. aurantium* L. Seville orange, *C. grandis* (L.) Osbeck, shaddock, pummelo, *C. maxima* (Burm.) Merr, ugli, *C. reticulata* Blanco x *C. sinensis* (L.) Osbeck, ortanique, *C. mitis* Blanco, calamondin, *Fortunella margarita* Lour. Swingle, kumquat (Rutaceae), *Amyris* P. Browne Rutaceae), *Zanthoxylum* L., *Zanthoxylum martinicense* (Lam.), *Lantana camara, Jatropha podagrica, Canna indica*, and *Z. pterota* L. (Rutaceae).

12. The method of claim 1, where in the toxin is derived from *Piper aduncum*.

13. The method of claim 1, where in the toxin is apiol.

14. A method of controlling the population size of a citrus-feeding swallowtail butterfly (*Heraclides andraemon*) species which naturally feeds on a plant of interest, comprising:
  (a) providing a host plant in a pretreatment state and selecting a chemical attractant extracted from the plant of interest which naturally attract the citrus-feeding swallowtail butterfly (*Heraclides andraemon*) species;
  (b) applying to the host plant the chemical attractant to attract the citrus-feeding swallowtail butterfly (*Heraclides andraemon*) species to the host plant and to cause the citrus-feeding swallowtail butterfly (*Heraclides andraemon*) species to lay eggs on the host plant; and
  (c) applying to the host plant or directly to the citrus-feeding swallowtail butterfly (*Heraclides andraemon*) species or the laid eggs an extract from *Piper* plant that contains a toxin that kills the citrus-feeding swallowtail butterfly (*Heraclides andraemon*) species,
  wherein a majority of the citrus-feeding swallowtail butterfly (*Heraclides andraemon*) species or the laid eggs die from ingesting or coming into contact with the extract.

15. The method of claim 14, wherein application of the extract or the chemical attractant consists of dipping, spraying, coating, diluting, covering, saturating, misting, fumigating, or dusting the host plant with the extract.

16. The method of claim 14, wherein the swallowtail butterfly species is selected from a group consisting of *Heraclides* (syn. *Papilio*) *andraemon* Hubner, *Heraclides andraemon: bonhotei* Sharpe, *Heraclides andraemon: andraemon* Hubner, *Heraclides andraemon: hernandezi* de la Torre, *Heraclides andraemon: tailori* Rothschild, and *Heraclides andraemon: tailori* Jordan.

17. The method of claim 14, wherein the host plant is a plant on which the swallowtail butterfly species naturally feeds in the wild.

18. The method of claim 14, wherein the host plant is a citrus plant.

19. The method of claim 14, wherein the host plant is one or more plants selected from the group consisting of *Citrus aurantifolia* (Christm.) Swingle (Rutaceae), *Piper amalago* var. *amalago* L. (Piperaceae), lime, *C. limon* (L.) Burm. F., lemon, *C. sinensis* (L.) Osbeck, sweet orange, *C. reticulata* Blanco, Mandarin orange, tangerine, *C. paradisi* Macf, grapefruit, *C. medica* L., citron, *C. aurantium* L. Seville orange, *C. grandis* (L.) Osbeck, shaddock, pummelo, *C. maxima* (Burm.) Merr, ugli, *C. reticulata* Blanco x *C. sinensis* (L.) Osbeck, ortanique, *C. mitis* Blanco, calamondin, *Fortunella margarita* Lour. Swingle, kumquat (Rutaceae), *Amyris* P. Browne Rutaceae), *Zanthoxylum* L., *Zanthoxylum martinicense* (Lam.), *Lantana camara, Jatropha podagrica, Canna indica*, and *Z. pterota* L. (Rutaceae).

20. The method of claim 1, where in the toxin is derived from *Piper aduncum*.

21. The method of claim 1, where in the toxin is apiol.

* * * * *